(12) United States Patent
Kinoshita et al.

(10) Patent No.: US 8,978,163 B2
(45) Date of Patent: Mar. 17, 2015

(54) PANT-TYPE WEARING ARTICLE AND METHOD FOR MAKING THE SAME

(75) Inventors: Akiyoshi Kinoshita, Kagawa (JP); Yasuhiko Kenmochi, Kagawa (JP)

(73) Assignee: Uni-Charm Corporation, Ehime (JP)

( * ) Notice: Subject to any disclaimer, the term of this patent is extended or adjusted under 35 U.S.C. 154(b) by 864 days.

(21) Appl. No.: 12/995,672

(22) PCT Filed: Apr. 20, 2009

(86) PCT No.: PCT/JP2009/057869
§ 371 (c)(1), (2), (4) Date: Dec. 2, 2010

(87) PCT Pub. No.: WO2009/147906
PCT Pub. Date: Dec. 10, 2009

(65) Prior Publication Data
US 2011/0072561 A1  Mar. 31, 2011

(30) Foreign Application Priority Data
Jun. 3, 2008  (JP) ................................. 2008-146312

(51) Int. Cl.
*A61F 13/15* (2006.01)
*A61F 13/49* (2006.01)
(Continued)

(52) U.S. Cl.
CPC ..... *A61F 13/49011* (2013.01); *A61F 13/15593* (2013.01); *A61F 13/49014* (2013.01); *A61F 13/4963* (2013.01); *A61F 13/15707* (2013.01);
(Continued)

(58) Field of Classification Search
USPC ...................................... 604/387, 391, 385.1
See application file for complete search history.

(56) References Cited

U.S. PATENT DOCUMENTS 5,032,122 A * 7/1991 Noel et al. ..................... 604/391
5,370,634 A * 12/1994 Ando et al. ............... 604/385.21
7,255,688 B2 * 8/2007 Sasaki et al. ................... 604/396
(Continued)

FOREIGN PATENT DOCUMENTS

EP  1 795 163 A1  6/2007
JP  6-52818  7/1994
(Continued)

OTHER PUBLICATIONS

International Search Report from corresponding PCT application No. PCT/JP2009/057869 dated Jul. 21, 2009, 4 pgs.
(Continued)

*Primary Examiner* — Richale Quinn
(74) *Attorney, Agent, or Firm* — Brinks Gilson & Lione (57) ABSTRACT

A pant-type wearing article configured so as to facilitate fastener members attached to inelastic regions defined in lateral zones of the wearing article to be handled. The pant-type wearing article includes front fastener members attached to transversely opposite lateral zones of a front waist region that are detachably engaged with rear fastener members attached to transversely opposite lateral zones of a rear waist region so as to form a pant-shaped wearing article. In the lateral zones, elastic members extending under tension in a circumferential direction across the waist regions are cut at a plurality of locations so as to form first front inelastic regions and first rear inelastic regions. The front fastener members and the rear fastener members are respectively attached to the first front inelastic regions and the first rear inelastic regions, respectively.

2 Claims, 6 Drawing Sheets

(51) Int. Cl.
*A61F 13/496* (2006.01)
*A61F 13/56* (2006.01)

(52) U.S. Cl.
CPC ... *A61F 13/5655* (2013.01); *A61F 2013/49036* (2013.01); *A61F 13/15756* (2013.01)
USPC .......................................... 2/69; 604/385.25

(56) References Cited

U.S. PATENT DOCUMENTS

| | | | |
|---|---|---|---|
| 7,727,215 B2 * | 6/2010 | Kenmochi et al. | 604/387 |
| 7,727,216 B2 * | 6/2010 | Kenmochi et al. | 604/389 |
| 8,206,365 B2 * | 6/2012 | Norrby | 604/385.22 |
| 8,337,479 B2 * | 12/2012 | Nilsson et al. | 604/387 |
| 8,545,473 B2 * | 10/2013 | Ichikawa et al. | 604/386 |
| 2003/0036739 A1 * | 2/2003 | Christoffel et al. | 604/385.3 |
| 2003/0055394 A1 * | 3/2003 | Gibbs | 604/389 |
| 2003/0135184 A1 * | 7/2003 | Van Gompel et al. | 604/385.01 |
| 2004/0230171 A1 | 11/2004 | Ando et al. | |
| 2004/0261230 A1 * | 12/2004 | Neeb et al. | 24/451 |
| 2005/0043698 A1 * | 2/2005 | Otsubo et al. | 604/385.25 |
| 2005/0043701 A1 * | 2/2005 | Otsubo et al. | 604/391 |
| 2005/0080394 A1 * | 4/2005 | Otsubo et al. | 604/385.27 |
| 2005/0132543 A1 * | 6/2005 | Lindsay et al. | 24/442 |
| 2005/0267431 A1 | 12/2005 | Sasaki et al. | |
| 2008/0009820 A1 * | 1/2008 | Kenmochi et al. | 604/389 |
| 2008/0249493 A1 * | 10/2008 | Kobayashi et al. | 604/378 |

FOREIGN PATENT DOCUMENTS

| | | |
|---|---|---|
| JP | 2002-253605 | 9/2002 |
| JP | 2005-095574 | 4/2005 |
| JP | 2005-261958 | 9/2005 |
| JP | 2006-087564 | 4/2006 |
| JP | 2006-087568 | 4/2006 |

OTHER PUBLICATIONS

European Supplementary Search Report from corresponding European application No. 09758173.0 dated Jan. 9, 2014 (7 pgs).

* cited by examiner

PANT-TYPE WEARING ARTICLE AND METHOD FOR MAKING THE SAME

RELATED APPLICATION

This application is a 35 U.S.C. §371 national phase filing of International Patent Application No. PCT/JP2009/057869, filed Apr. 20, 2009, through which and to which priority is claimed under 35 U.S.C. §119 to Japanese Patent Application No. 2008-146312, filed Jun. 3, 2008.

TECHNICAL FIELD

The present invention relates to pant-type wearing articles suitable to be used as disposable diapers or disposable toilet-training pants and also to methods for making the same.

RELATED ART

Various designs have already been proposed for pant-type wearing articles having front and rear waist regions adapted to be connected with each other along respective pairs of transversely opposite lateral zones thereof via a fastener in a manner that these lateral zones may be unfastened and, if desired, refastened. For example, a disposable absorbent article disclosed in JP 2005-95574 A (PATENT DOCUMENT 1) is provided along the respective pairs of transversely opposite lateral zones of front and rear waist regions with fastener members each extending from a peripheral edge of a waist opening to respective peripheral edges of leg-openings. The fastener members provided along the lateral zones of the front waist region are engaged with the associated fastener members provided along the lateral zones of the rear waist region to achieve a desired function as the fastener. During a production process for this absorbent article, the respective lateral zones of the front and rear waist regions along which these fastener members are attached are pre-treated to become inelastic. To obtain such inelastic lateral zones, respective elastic members extending under tension across the front and rear waist regions in initial several steps are left contract only along the lateral zones in the subsequent step using a known snap-back technique.
[PATENT DOCUMENT 1] JP 2005-95574 A

DISCLOSURE OF THE INVENTION

Problem to be Solved by the Invention

In the case of the absorbent article disclosed in PATENT DOCUMENT 1, the elastic members sandwiched between the inner sheet and the outer sheet must be left contract only in the lateral zones in order to make these lateral zones inelastic. To assure that these elastic members can be easily and reliably left contract, it is impermissible to bond the inner and outer sheets to each other integrally over a large area. In other words, respective regions of the inner and outer sheets defining these lateral zones are incompletely bonded to each other and, in consequence, may freely move with respect to each other. These relatively movable lateral zones bearing the fastener members are inconvenient when it is tried to hold these lateral zones with the fingers and thereby to handle the fastener members. In addition, during the production process for this wearing article, a schedule control inevitably becomes complex in view of the restriction that the regions of the inner and outer sheets defining the lateral zones should not be coated with adhesive when the inner and outer sheets are bonded to each other.

In view of the problems as have been described above, it is an object of the present invention to improve such conventional wearing article and a method for making the same.

Measure to Solve the Problem

The object set forth above is achieved by an improvement in the pant-type wearing article according to the present invention on a first aspect thereof and by an improvement in a method for making the same according to the present invention on a second aspect thereof.

On the first aspect of the present invention, the present invention relates to the pant-type wearing article comprising a first waist region defined by one of front and rear waist regions, a second waist region defined by the other of front and rear waist regions and a crotch region extending between these first and second waist regions wherein respective inner surfaces of second fastener members provided along transversely opposite lateral zones of the second waist region are detachably engaged with respective outer surfaces of first fastener members provided along transversely opposite lateral zones of the first waist region to obtain the pant-type wearing article having a waist-opening and a pair of leg-openings formed upon the engagement.

The improvement in the wearing article according to the present invention on the first aspect thereof is characterized in that at least one waist region of the first waist region and the second waist region includes a plurality of elastic members extending under tension across the one waist region and, in the transversely opposite lateral zones, each of the elastic members is cut off at a plurality of locations along its length to form an inelastic regions being neither elastically stretchable nor elastically contractible and the first fastener member or the second fastener members provided in the one waist region are formed in the inelastic regions.

According to one preferred embodiment of the present invention on this first aspect, the respective elastic members are cut off also in regions spaced inward from the inelastic regions formed in the transversely opposite lateral zones as viewed in a waistline direction of the one waist region.

On the second aspect of the present invention, the object set forth above is achieved by an improvement in a method for making the wearing article according to the present invention on the first aspect thereof, the method being improved so as to comprise the steps to form inelastic regions in a web initially being stretchable and contractible in a machine direction as follow:

a. continuously feeding, in the machine direction, a composite web comprising first and second webs put flat and bonded together so as to extending in the machine direction and a plurality of elastic members sandwiched between the first and second webs so as to extend in the machine direction and bonded to at least one of the first and second webs;

b. cyclically and locally subjecting the composite web fed in the machine direction to action of a cutter and thereby cutting off the elastic members in predetermined regions of the composite web to convert the predetermined ranges to inelastic regions; and c. bonding a female or male component of a mechanical fastener to one of the first and second webs in each of the inelastic regions.

According to one preferred embodiment of the present invention on the second aspect thereof, the method further includes a step of cutting off respective the elastic members also in second predetermined regions spaced from the predetermined regions.

According to another preferred embodiment of the present invention on the second aspect thereof, the first and second webs and the elastic members are bonded together by adhesive in the predetermined regions.

Effect of the Invention

In the pant-type wearing article and the method for making the same according to the present invention, the inelastic regions in at least one of the first waist region and the second waist region provided with the first fastener members or the second fastener members are formed by cutting off the respective elastic members at a plurality of locations in the longitudinal direction thereof. This means that the sheet members put flat together may be bonded to each other in the lateral zones in which the inelastic regions are to be formed before the elastic members are cut off. Therefore the first fastener members or the second fastener members attached to the associated lateral zones would not be prevented from being smoothly handled because of the sheet members put flat together in these lateral zones which are freely movable with respect to each other. On the aspect relating to the method for making this wearing article, adhesive by which the sheet members put flat together are bonded to each other can be applied also to the regions allocated to define the lateral zones of the first and second waist regions just as to the remaining regions. In this way, the process control for the wearing article is correspondingly facilitated.

IDENTIFICATION OF REFERENCE NUMERALS USED IN THE DRAWINGS 1 absorbent article (diaper)
6 front waist region
7 rear waist region
8 crotch region
11 lateral zone (front lateral zone)
12 first fastener member (front fastener member)
13 lateral zone (rear lateral zone)
14 second fastener member (rear fastener member)
16 elastic member
17 elastic member
18 elastic member
36 elastic member
37 elastic member
51 inelastic region
52 second inelastic region
61 inelastic region
62 second inelastic region
116 elastic member
117 elastic member
118 elastic member
136 elastic member
137 elastic member
160 cutter
171 web (first composite web)
5 MD machine direction

DETAILED DESCRIPTION OF THE PREFERRED EMBODIMENTS

A pant-type wearing article and a method for making the same will be described hereunder in more details with reference to the accompanying drawings.

Figure 1:
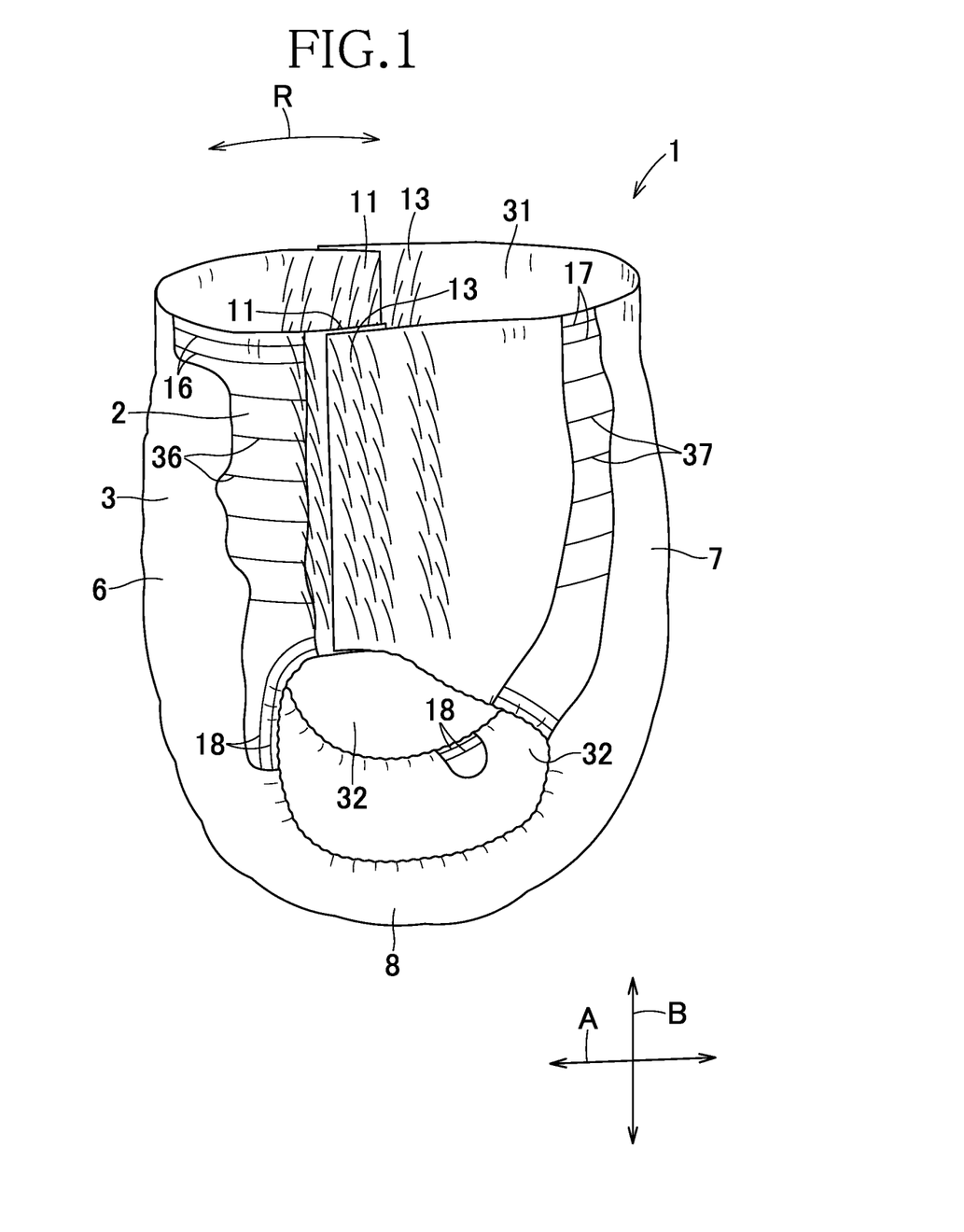
FIG. 1 is a side view showing the diaper as partially broken away.
Figure 2:
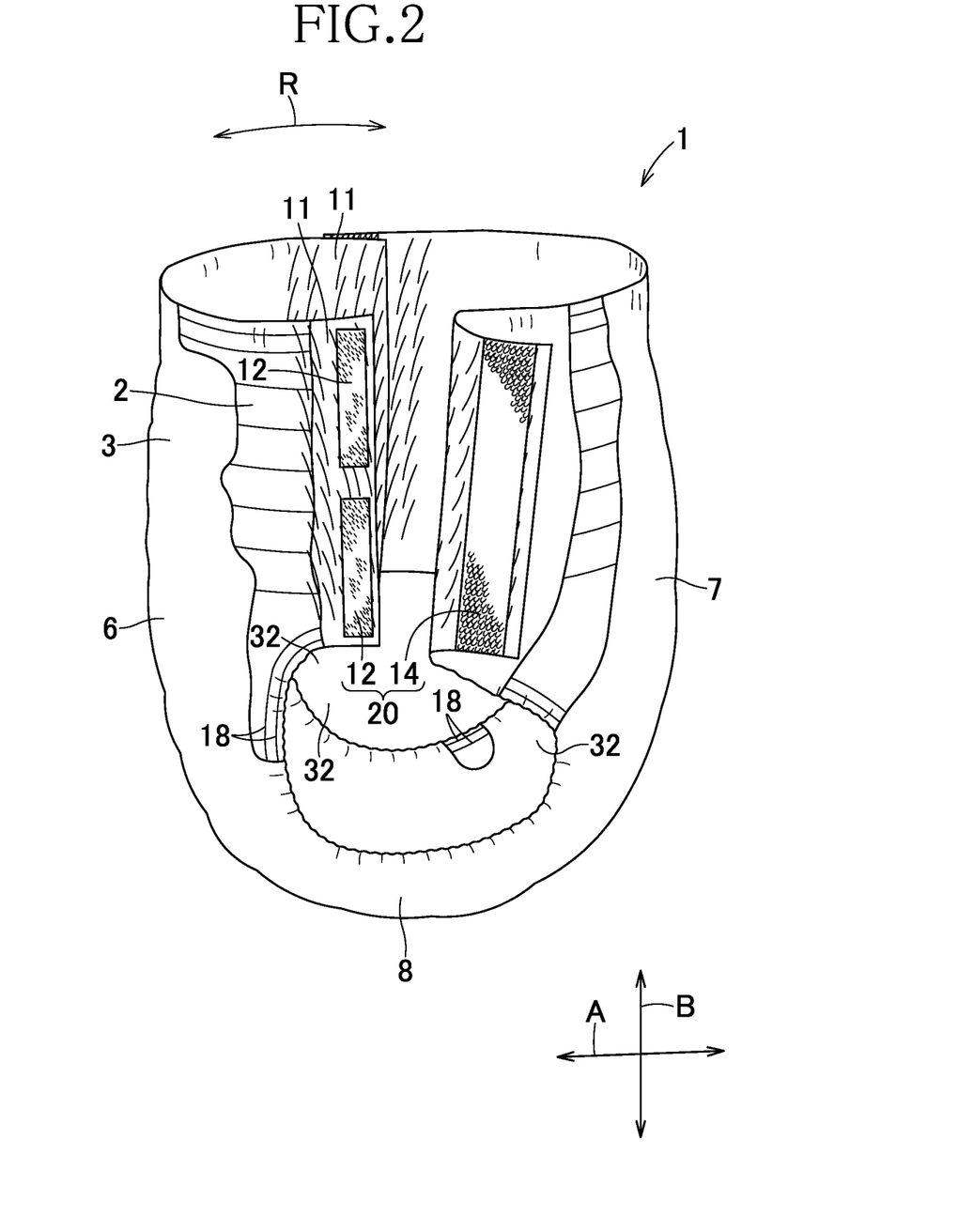
FIG. 2 is a view similar to FIG. 1, showing the diaper having one of lateral zones thereof opened.

FIG. 1 is a partially cutaway side view showing a diaper 1 as an example of a pant-type wearing article according to the present invention and FIG. 2 is a partially cutaway side view showing the diaper 1 having one of lateral zones thereof opened. A front-back direction, a vertical direction and a circumferential direction are indicated by double-headed arrows A, B and R, respectively. The diaper 1 has a front waist region 6, a rear waist region 7 and a crotch region 8 extending between these two waist regions 6, 7. These regions 6, 7 and 8 respectively comprise a liquid-pervious inner sheet 2, a liquid-impervious outer sheet 3 and a body fluid absorbent core 4 (See FIG. 3) sandwiched between these two sheets 2, 3. In the front waist region 6, front lateral zones 11 opposite in the waistline direction R and extending in the vertical direction B are provided on respective outer surfaces thereof with front fastener members 12 attached thereto (See FIG. 2). In the rear waist region 7, rear lateral zones 13 opposite in the waistline direction R and extending in the vertical direction B are provided with rear fastener members 14 attached thereto. The inner sheet 2 is formed, for example, of a nonwoven fabric made of thermoplastic synthetic fibers and the outer sheet 3 is formed, for example, of a thermoplastic synthetic resin film, a nonwoven fabric made of thermoplastic fibers or a composite sheet comprising these film and nonwoven fabric.

The front fastener members 12 are associated with the rear fastener members 14 to form fasteners 20 for connecting the front and rear waist regions 6, 7 in a manner that these waist regions are able to be unfastened and refastened, respectively, wherein the hook members constituting the mechanical fastener widely known in the trade name of Magic Tape are used here as the front fastener members 12 and the loop members constituting this mechanical fastener are used here as the rear fastener members 14. FIG. 1 shows the diaper 1 wherein a pair of front lateral zones 11 is connected with a pair of the associated rear lateral zones 13 via the fasteners 20 and FIG. 2 shows the diaper 1 wherein a pair of front lateral zones 11 is connected with a pair of the associated rear lateral zones 13 via the fasteners 20 on the remote side and a pair of front lateral zones 11 has been disengaged from the associated rear lateral zones 13 on the near side. Obviously, the pant-type disposable diaper according to the invention can be put on and taken off from the wearer in the same manner as the diaper of prior art. The diaper according to the invention is distinguished from the diaper of prior art in that it is easy for the inventive diaper to open one of the lateral zones and thereby to check whether urination and/or defecation has occurred or not even when the wearer is in upright posture. This advantage can be effectively utilized by the user particularly when the diaper is delivered to the user in the pants-shape.

Referring to FIG. 1, the front and rear waist regions 6, 7 are detachably connected to each other and thereupon a waist-opening 31 and a pair of leg-openings 32 are formed, in other words, the diaper 1 is shaped into a pant. The front fastener members 12 and the rear fastener members 14 which consist fastener 20 respectively extend from the waist-opening 31 to the leg-openings 32. It should be noted that, in the illustrated embodiment, the front fastener members 12 are respectively divided into upper and lower portions.

Figure 3:
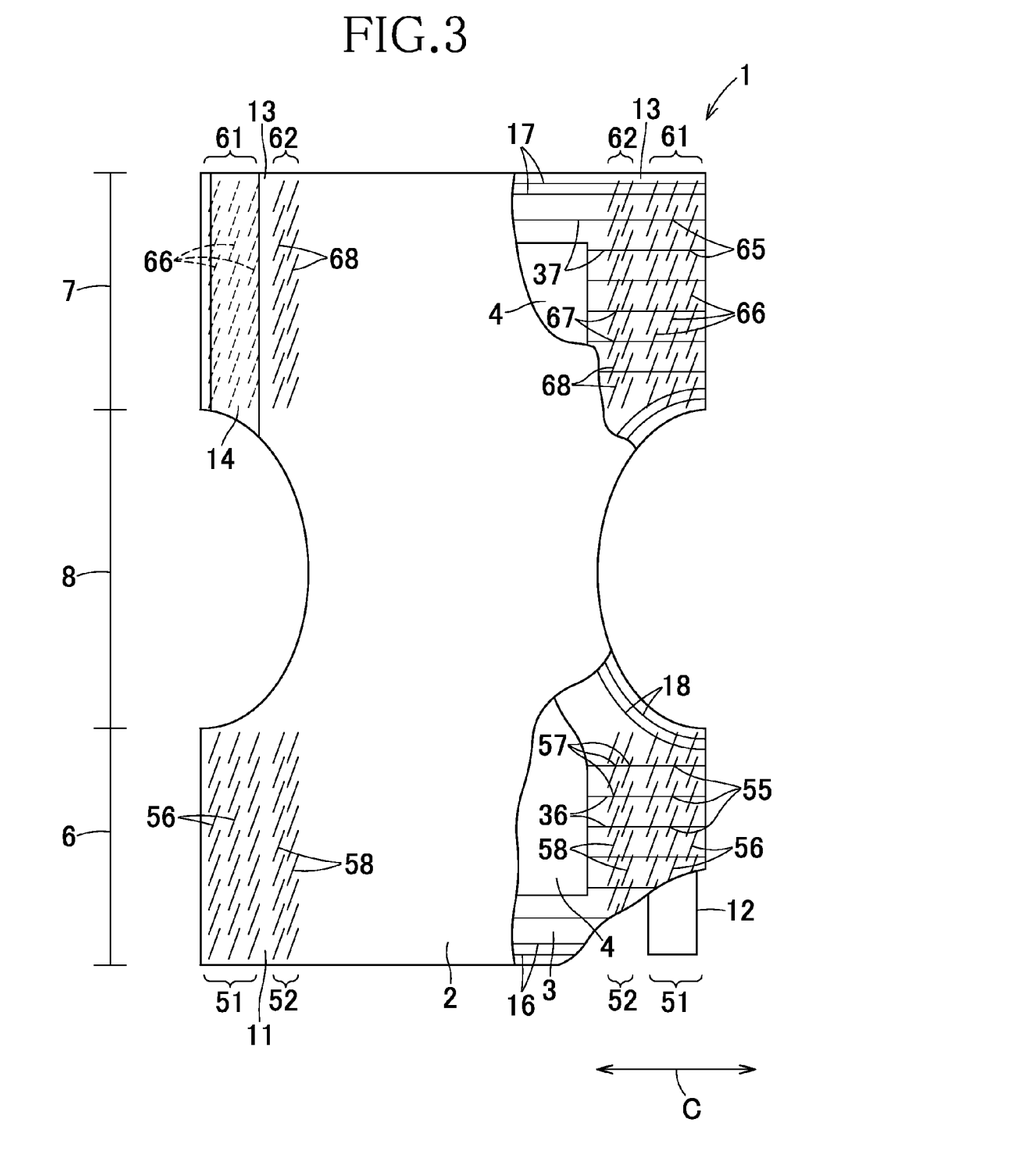
FIG. 3 is a partially cutaway plan view showing the diaper as the front waist region and the rear waist region thereof have been disconnected from each other and flatly developed.

FIG. 3 is a partially cutaway plan view of the diaper 1 with the front waist region 6 and the rear waist region 7 having been connected together via the fasteners 20 in the phase of FIG. 1 being disengaged from each other and flatly developed wherein a transverse direction of the front and rear waist regions 6, 7 is indicated by a double-headed arrow C. In the diaper 1 shown in FIG. 3, the core 4 illustrated herein as partially broken away has a concave shape curved inwardly. The inner and outer sheets 2, 3 sandwich the core 4 therebetween extend outward beyond a peripheral edge of the core 4 and bonded to each other in these portions extending outward by hot melt adhesive (not shown) coated intermittently and evenly on these portions. These portions of the inner and outer sheets 2, 3 extending outward include the front lateral zones 11 and the rear lateral zones 13. The inner and outer sheets 2, 3 are bonded also to upper and lower surfaces of the core 4 by hot melt adhesive (not shown).

Various elastic members are sandwiched between the inner and outer sheets 2, 3. Specifically, the front waist region 6 is provided with waist elastic members 16 extend under tension in the transverse direction C, the rear waist region 7 is provided with waist elastic members 17 extending under tension in the transverse direction C and the crotch region 8 is provided with leg elastic members 18 extending under tension so as to describe curves along respective peripheral edges of the leg-openings 32. In addition to these elastic members, front intermediate elastic members 36 are provided between the front waist elastic members 16 and the leg elastic members 18 so as to extend under tension in the transverse direction C and rear intermediate elastic members 37 provided between the rear waist elastic members 17 and the leg elastic members 18 so as to extend under tension in the transverse direction C. These elastic members 16, 17, 18, 36, 37 are intermittently bonded over full lengths thereof to the inner sheet 2 and/or the outer sheet 3 by hot melt adhesive wherein the elastic members 16, 36 extend across the front waist region 6 and the elastic members 17, 37 extend across the rear waist region 7. The front and rear waist regions 6, 7 are stretched and contracted in the transverse direction C, in other words, in the waistline direction R in FIG. 1 as these elastic members 16, 17, 36, 37 are stretched and contracted, respectively. It should be noted here that the front lateral zones 11 of the front waist region 6 are respectively formed with first front inelastic regions 51 and second front inelastic regions 52. Similarly, the rear lateral zones 13 of the rear waist region 7 are respectively formed with first rear inelastic regions 61 and second rear inelastic regions 62.

The first front inelastic regions 51 include the front waist elastic members 16 extending across the front waist region 6, the front intermediate elastic members 36 extending also across the front waist region 6 and the leg elastic members 18. Of these elastic members 16, 36, 18, at least the elastic members 16, 36 may be cut at a plurality of points 55 along length thereof to form the first front inelastic regions 51. In consequence, these first front inelastic regions 51 are neither elastically stretched nor elastically contract. To cut these elastic members 16, 18, 36, cutter blades may be pressed against one of the inner sheet 2 and the outer sheet 3 from the outer side to form a plurality of cuts 56. Pieces of the elastic members 16, 18, 36 created by this cutting operation remain in the first front inelastic regions 51. Each of these first inelastic regions 51 is preferably dimensioned to be the same as or slightly larger than a size of the front fastener member 12 attached to the first inelastic region 51. In this way, the front fastener members can be prevented from gathering under contraction of the elastic members 16, 18, 36 and, in consequence, an engagement area between the front fastener members 12 and the associated rear fastener members 14 might be substantially reduced.

The second front inelastic regions 52 are formed aside inward from the associated first front inelastic regions 51 as viewed in the transverse direction C and preferably spaced from the associated first front inelastic regions 51 by a distance in a range of 5 to 15 mm. The second front inelastic regions 52 are formed by cutting at least the elastic members 16, 36 of these elastic members 16, 18, 36 each at a single point 56 along with cuts 58. The presence of these second front inelastic regions 52 effectively eliminate a possibility that the front fastener members 12 might be directly pulled by at least the elastic members 16, 36 of these elastic members 16, 18, 36 in the waistline direction R when the front waist region 6 and the rear waist region 7 are repetitively connected with and disconnected from each other. It should be understood here that the present invention may be exploited without forming the second front inelastic regions 52 unless such effective function of the second front inelastic regions 52 is required.

The first rear inelastic regions 61 include the rear waist elastic members 17 extending across the rear waist region 7, the rear intermediate elastic members 37 extending also across the rear waist region 7 and the leg elastic members 18. Of these elastic members 17, 37, 18, at least the elastic members 17, 37 may be cut at a plurality of points 65 along length thereof to form the first rear inelastic regions 61. In consequence, these first rear inelastic regions 61 can be neither elastically stretched nor elastically contracted. These elastic members 17, 18, 37 may be cut by the cutter blade in the same manner as in the case of the elastic members 16, 18, 36. Each of these first rear inelastic regions 61 is preferably dimensioned to be same as or slightly larger than a size of the rear fastener member 14 attached to the first inelastic region 61. In this way, the rear fastener members 14 can be prevented from being formed with gathers undulating in the waistline direction R. The second rear inelastic regions 62 are formed aside inward from the associated first rear inelastic regions 61 and preferably spaced from the associated first rear inelastic regions 61 by a distance in a range of 5 to 15 mm. The second rear inelastic regions 62 are formed by cutting at least the elastic members 17, 37 of these elastic members 17, 18, 37 each at least a single point 66 along with cuts 68. The presence of these second rear inelastic regions 62 effectively eliminate a possibility that the rear fastener members 14 might be directly pulled by the elastic members 17, 18, and 37 in the waistline direction R when the front waist region 6 and the rear waist region 7 are repetitively connected with and disconnected from each other. It should be understood here that the present invention may be exploited without forming the second rear inelastic regions 62 unless such effective function of the second rear inelastic regions 62 is required.

While the front fastener member 12 is divided into upper and lower halves according to the particular embodiment of the invention shown by FIG. 1 so that the front lateral zones 11 may be easily deformed between the upper and lower halves of the respective front fastener members 12 and thereby may provide a good fit to the wearer's body, the front fastener members 12 each divided into the upper and lower halves may be replaced by the not divided but continuous front fastener members 12 unless such effect is required. While the rear fastener members 14 is implemented in the form of the loop members adapted to be engaged with the associated front fastener members 12 in the illustrated embodiment, the inner sheet 2 to which these rear fastener members 14 are attached may replace the rear fastener members 14 so far as the inner sheet 2 can be repetitively engaged with and disengaged from the associated front fastener members. Regarding the fasteners 20 in the illustrated embodiment, it is possible to use the loop members of the mechanical fastener as the front fastener members 12 and to use the hook members adapted to be engaged with the associated loop members as the rear fastener members 14. Furthermore, it is also possible to attach the front fastener members 12 to the inner surface of the front lateral zones 11 and to attach the rear fastener member 14 to the inner surface of the rear lateral zones 13.

Figure 4:
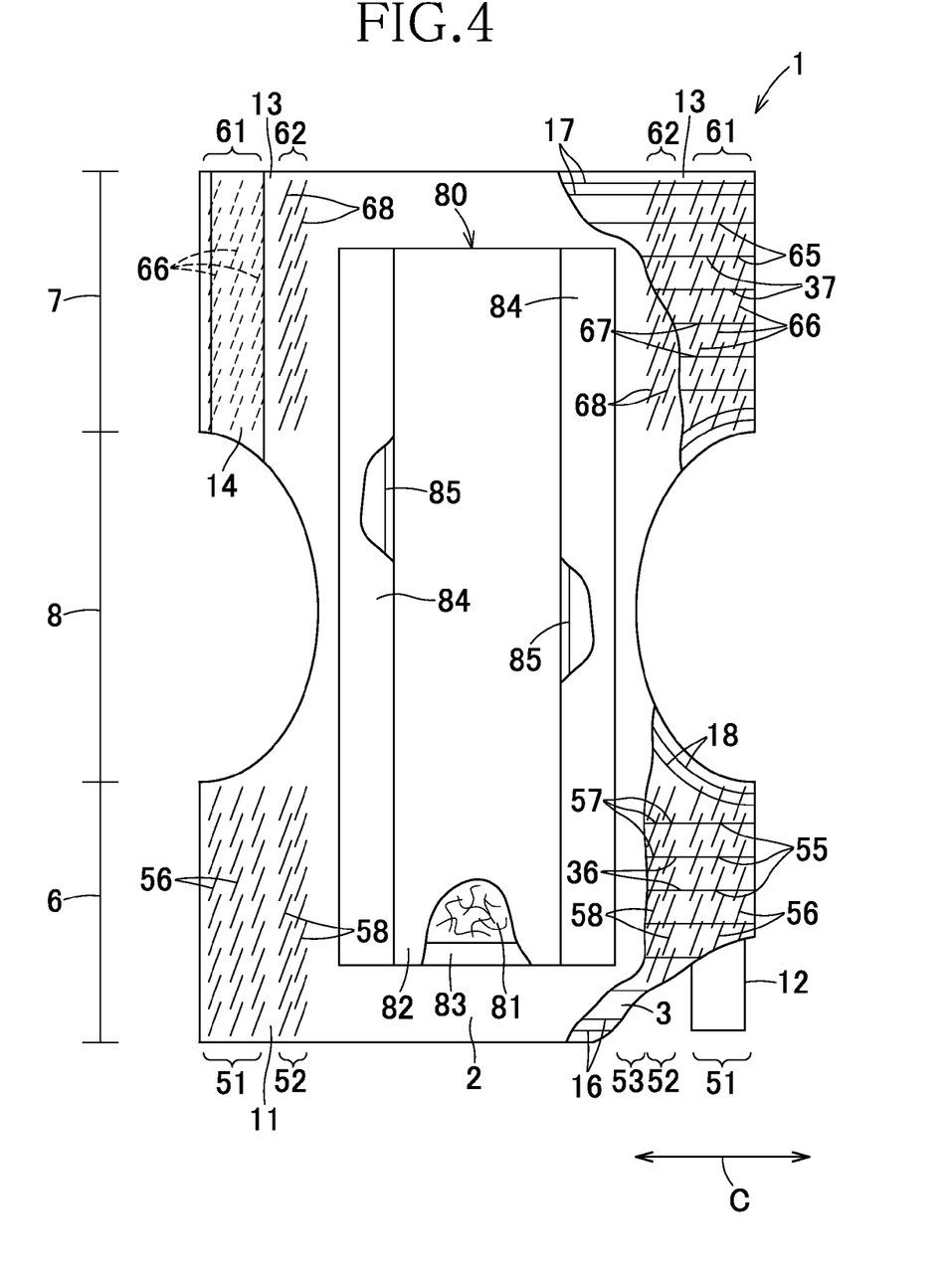
FIG. 4 is a view similar to FIG. 3, showing one preferred embodiment of the invention.

FIG. 4 is a view similar to FIG. 3, showing one preferred embodiment. In the diaper 1 shown in FIG. 4 as has been flatly developed diaper 1, the core 4 in FIG. 3 is replaced by a body fluid absorbent panel 80 attached to the inner surface of the inner sheet 2. The panel 80 comprises a body fluid absorbent core 81, a liquid-pervious sheet 82 covering the upper surface of the core 81 and a liquid-impervious thermoplastic synthetic resin film is sandwiched between the core 81 and the inner sheet 2. The panel 80 is provided along transversely opposite side edges thereof with leak-barriers 84 themselves well known art, respectively. With the diaper 1 put on the wearer's body these leak-barriers 84 raise themselves from the panel 80 toward the wearer's skin so that these leak-barriers 84 would be held in contact with the wearer's thighs with fitness required to prevent body fluids from leaking sideways. Each of the leak-barriers 84 includes an elastic member 85 extending under tension in the longitudinal direction of the leak-barrier 84. In this diaper 1, the inner sheet 2 and the outer sheet 3 are bonded to each other by adhesive (not shown) coated on these sheets 2, 3 so as to be uniformly distributed thereon. According to this embodiment also, the elastic members 16, 17, 18, 36, 37 are attached under tension so as be sandwiched between these sheets 2, 3 and, similarly to the embodiment shown in FIG. 3, the front lateral zones 11 and the rear lateral zones 13 are formed with the first and second front inelastic regions 51, 52 and the first and second rear inelastic regions 61, 62, respectively. The front fastener members 12 are attached to the first front inelastic regions 51 and the rear fastener members 14 are attached to the first rear inelastic regions 61. To make such diaper 1, a composite sheet consisting of the inner and outer sheets 2, 3 put flat and bonded together may be previously prepared and then the panel 80 may be attached to such composite sheet by adhesive. The embodiment shown in FIG. 4 is distinguished from the embodiment shown in FIG. 3 in that it is possible to use a liquid-impervious plastic film as the inner sheet 2.

Figure 5:
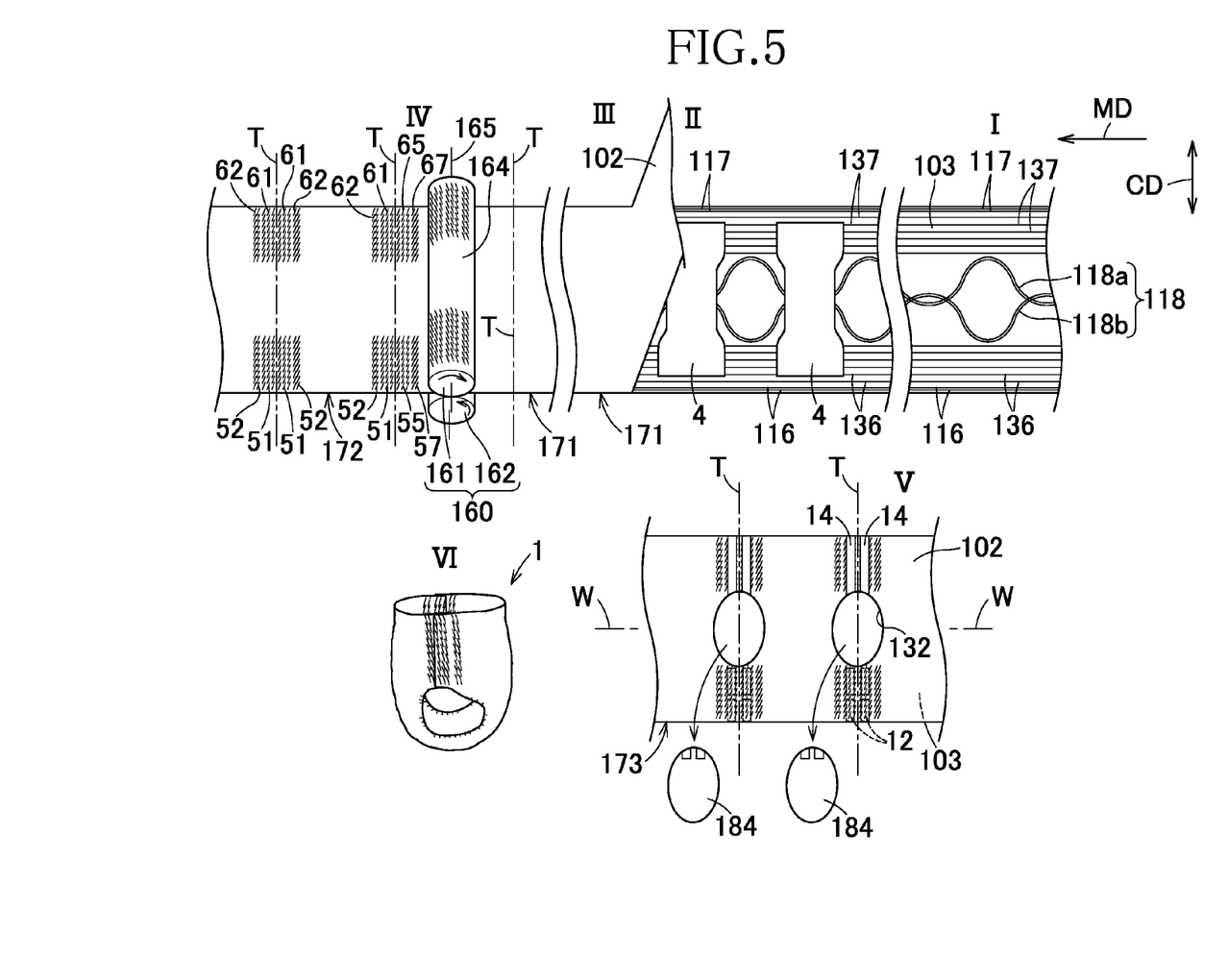
FIG. 5 is a diagram schematically illustrating a production process for the diaper.

FIG. 5 is a schematic diagram partially illustrating a production process for the diaper 1 shown in FIG. 1 wherein a machine direction is indicated by an arrow MD and a direction orthogonal to the machine direction MD is indicated by a double-headed arrow CD.

Referring to FIG. 5, in a step I, respective continuous materials 116, 117, 118, 136 and 137 for the front waist elastic members 16, the rear waist elastic members 17, the leg elastic members 18, the front intermediate elastic members 36 and the rear intermediate elastic members 37 are attached to a web 103 which is continuous material for the outer sheet 3 being fed in the machine direction MD by hot melt adhesive (not shown). The continuous material 118 for the leg elastic members 18 comprises continuous material 118*a* and continuous material 118*b* describing sine curves intersecting with each other.

In a step II, the panel-like body fluid absorbent cores 4 are at intervals attached to the web 103 at predetermined locations thereon as viewed in the machine direction MD by hot melt adhesive (not shown).

In a step III, web 102 which is continuous material for the inner sheet 2 is fed in the machine direction MD so as to cooperate with the web 103 to sandwich the continuous materials 116, 117, 118, 136, 137 of the respective elastic members and the individual cores 4. Specifically, the web 103 and the web 102 are put flat and bonded together by hot melt adhesive (not shown) intermittently and uniformly coated on one of these two webs 102, 103 to form first composite web 171. This first composite web 171 is elastically stretchable and contractible in the machine direction MD.

In a step IV, the first composite a web 171 is fed into a roll nip defined between a first roll 161 and a second roll 162 cooperating together to form a cutter 160 and thereby the continuous materials 116, 117, 118, 136 and 137 for the respective elastic members are locally cut in a region defined between each pair of the adjacent cores 4, 4. In this way, the step IV results in formation of second composite web 172 having a plurality of cuts 55, 56, 65, 66 as seen in FIG. 3, the first and second front inelastic regions 51, 52 cyclically arranged in the machine direction MD and the first and second rear inelastic regions 61, 62 cyclically arranged in the machine direction MD in a manner similar to the first and second front inelastic regions 51, 52.

In a step V, the front fastener members 12 shown by FIG. 1 are attached to the web 102 constituting the second composite web 172 in the first front inelastic regions 51 while the rear fastener members 14 are attached to the web 103 constituting the second composite web 172 in the first rear inelastic regions 61. The step V further includes a sub-step of cutting out disc-like laminate 184 consisting of the webs 102, 103 put flat and bonded together from the second composite web 172 between each pair of the adjacent cores 4 to obtain third composite web 173 formed with openings 132.

In a step VI, the third composite web 173 is cut along respective center lines T (See the step V) extending in the cross direction CD between each pair of the adjacent cores 4, 4 and the rear fastener members 14 are engaged with the associated front fastener members 12 to obtain the individual pant-like diapers 1. By cutting the third composite web 173 in this manner, the first and second front inelastic regions 51, 52 and the first and second rear inelastic regions 61, 62 are obtained on both sides of the respective center lines T. At the same time, the openings 132 are respectively bisected so as to form the respective peripheral edges of the leg-openings 32.

Figure 6:
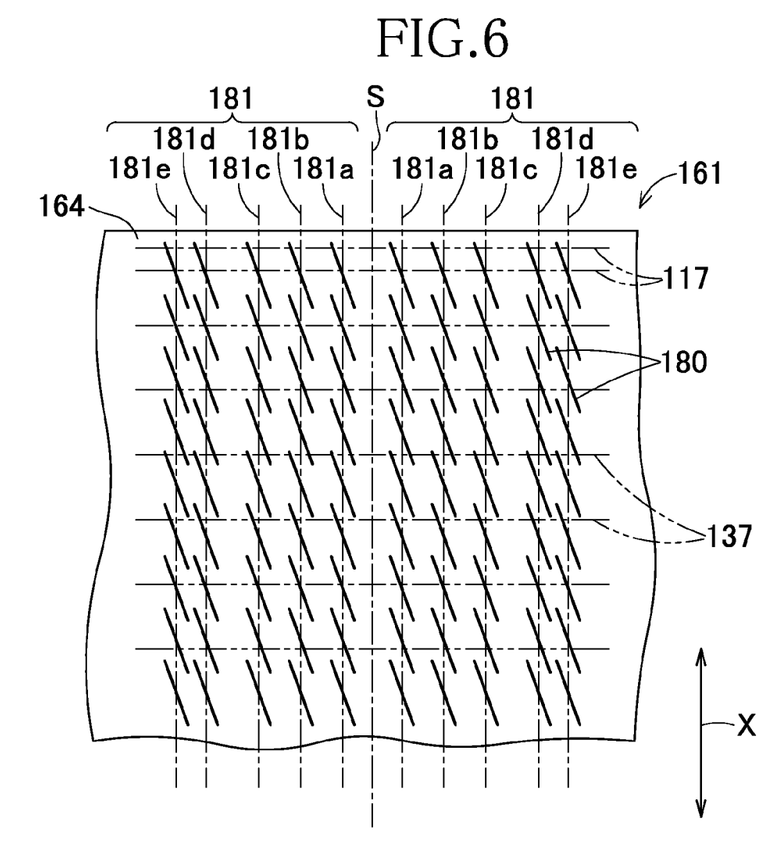
FIG. 6 is a partial view of the first roll.

FIG. 6 illustrates a portion of the first roll 161 constituting the cutter 160 used in the production process illustrated in FIG. 5 as has been flatly developed. The first roll 161 is used with a second roll 162 having a smooth peripheral surface (not shown) wherein some (117, 137) of the elastic members to be cut by the cutter 160 are indicated by imaginary lines. The first roll 161 is formed on the peripheral surface 164 thereof with a plurality of blade segments 180. These blade segments 180 radially project from the peripheral surface 164 and to serve to cut the respective continuous materials 116, 117, 118, 136 and 137 lying between these blade segments 180 and a peripheral surface of the second roll 162 under a pressure with or without heating. Such blade segments 180 are arranged intermittently in an axial direction X of the first roll 161 to form a blade array 181. The first roll 161 has a plurality of the blade arrays 181 and, in FIG. 6, first through fifth pairs of blade arrays 181*a* through 181*e* are arranged so as to be symmetric one with another about an imaginary line S extending in the axial direction X. It should be noted that the individual blade segments 180 included in each of the blade arrays on the first roll 161 are spaced one from another substantially at regular intervals and oblique in a common direction and at a common angle with respect to the axial direction X. Furthermore, the individual blade segments 180 in each of the blade arrays 181 are uniquely arranged. Specifically, assumed that these individual blade segments 180 are moved in a circumferential direction, each pair of the blade segments adjacent in the axial direction X will partially overlap and provide the same effect as a single blade continuously extending in the axial direction X will provide. Consequentially, it is assured that the respective continuous materials 116, 117, 118, 136 and 137 for the respective elastic members extending in the machine direction MD are cut by these blade arrays.

On the peripheral surface of the first roll 161, the first, second and third blade arrays 181a, 181b and 181c successively adjacent in the circumferential direction are used to form the diaper 1 with the first front inelastic regions 51 and the first rear inelastic regions 61. The fourth and fifth blade arrays 181d and 181e are used to form the diaper 1 with the second front inelastic regions 52 and the second rear inelastic regions 62.

The blade segments 180 may be heated at a desired temperature to facilitate the continuous materials 116, 117, 118, 136 and 137 for the respective elastic members to be cut, on one hand, and to melt-solidify regions of nonwoven fabric or film forming the web 102 and the web 103 in contact with the blade segments 180, on the other hand. The second roll 162 also is adapted to be adjustably heated at a desired temperature. A distance by which the first roll 161 and the second roll 162 are spaced from each other is adjustable. Even under such conditions, the web 102 and/or the web 103 might be damaged when the continuous materials 116, 117, 118, 136, 137 for the respective elastic members are cut by the blade segments 180. In such a case, the component fibers forming the nonwoven fabric might be drawn apart and/or break or tear of the film-like sheet might propagate in the course of the cutting operation. However, the regions of the nonwoven fabric or the film-like sheet being in contact with the blade segments 180 and/or the pins 190 may be melt-solidified to prevent such damage from propagating.

The method according to the invention designed to form the first front inelastic regions 51 and the first rear inelastic regions 61 as has been described just above advantageously allows to coat the web 102 and/or the web 103 with hot melt adhesive intermittently and uniformly to bond these webs 102, 103 to each other. In other words, it is unnecessary to provide adhesive-free regions as the inelastic regions.

The method exemplarily illustrated in FIG. 5 as well as the first roll 161 exemplarily illustrated in FIG. 6 may be appropriately varied depending on the particular shape and/or construction of the diaper 1. For example, it is possible to change the step V so that the front fastener members 12 and the rear fastener members 14 maybe folded back onto each other along a center line W (See FIG. 5) bisecting the width thereof to obtain the diaper 1 flatly folded having the first and second fastener members in engaged state. Furthermore, it is also possible to change the number of the blade arrays 181, the distance between each pair of the blade arrays 181 adjacent in the circumferential direction, the length of the individual blade segments 180 in the blade array 181, the inclination angle of the individual blade segments 180 with respect to the axial direction X, and the distance between each pair of the adjacent blade segments 180. In addition, according to the invention, the order in which the first composite web is formed with the first and second front inelastic regions 51, 52 and the first and second rear inelastic regions 61, 62 is not specified. For example, after the first composite web 171 has been formed with the front inelastic regions 51 and the first rear inelastic regions 61 by using the first and second rolls 161, 162, it is possible to form the second front inelastic regions 52 and the second rear inelastic regions 62 by using a pair of rolls independent from the first and second rolls 161, 162.

The present invention as has been described on the basis of the disposable diaper as the typical example may be implemented also, for example, in the form of toilet-training pants, incontinent briefs or disposable pants.

The invention claimed is:

1. A pant-type wearing article comprising:
    a first waist region defined by one of front and rear waist regions;
    a second waist region defined by the other of said front and rear waist regions;
    a crotch region extending between said first and second waist regions;
    each said first waist region, second waist region and crotch region including an inner sheet and an outer sheet,
    second fastener members provided along transversely opposite lateral zones of said second waist region which have inner surfaces;
    first fastener members provided along transversely opposite lateral zones of said first waist region which have outer surfaces;
    said inner surfaces of said second fasteners members being detachably engaged with the outer surfaces of said first fasteners members so as to form the pant-type wearing article having a waist-opening and a pair of leg-openings formed upon the engagement;
    at least one waist region of said first waist region and said second waist region includes a plurality of elastic members extending under tension across said one waist region which are sandwiched between said inner sheet and said outer sheet and, in said transversely opposite lateral zones, each of said elastic members together with adjacent portions of said inner sheet and said outer sheet are cut through at a plurality of locations along its length obliquely at predetermined intervals in a longitudinal direction of the pant-type article to form an inelastic regions being neither elastically stretchable nor elastically contractible; and
    said first fastener members or said second fastener members provided in said one waist region are formed in said inelastic regions.

2. The wearing article as defined by claim 1, wherein said respective elastic members are cut off also in regions spaced inward from said inelastic regions formed in said transversely opposite lateral zones as viewed in a waistline direction of said one waist region.

* * * * *